United States Patent [19]

Graham et al.

[11] Patent Number: 4,814,182

[45] Date of Patent: Mar. 21, 1989

[54] CONTROLLED RELEASE DEVICE

[75] Inventors: Neil B. Graham, Bearsden; Marion E. McNeill, Milngavie; David A. Wood, Carluke, all of Scotland

[73] Assignee: National Research Development Corporation, London, England

[21] Appl. No.: 39,805

[22] Filed: Apr. 15, 1987

Related U.S. Application Data

[63] Continuation of Ser. No. 889,309, Jul. 28, 1986, abandoned, which is a continuation of Ser. No. 633,459, Jul. 23, 1984, abandoned.

[30] Foreign Application Priority Data

Jul. 22, 1983 [GB] United Kingdom ............... 8319766

[51] Int. Cl.⁴ ........................... A61K 9/00; C08J 3/08
[52] U.S. Cl. .................................. 424/484; 424/425; 424/486
[58] Field of Search ........................ 424/425, 484, 486

[56] References Cited

U.S. PATENT DOCUMENTS

| 3,924,622 | 12/1975 | Brooke | 424/467 |
|---|---|---|---|
| 4,014,335 | 3/1977 | Arnold | 424/21 |
| 4,203,442 | 5/1980 | Michaels | 604/892 |
| 4,220,152 | 9/1980 | Dresback | 604/892 |
| 4,308,867 | 1/1982 | Roseman et al. | 424/16 |
| 4,438,258 | 3/1984 | Graham | 524/593 |
| 4,451,260 | 5/1984 | Mitra | 424/21 |
| 4,542,176 | 9/1985 | Graham | 524/548 |

FOREIGN PATENT DOCUMENTS

| 00291 | 1/1979 | European Pat. Off. . |
|---|---|---|
| 0016654 | 10/1980 | European Pat. Off. . |
| 2047093 | 11/1980 | United Kingdom . |
| 2047094 | 11/1980 | United Kingdom . |
| 2090264 | 7/1982 | United Kingdom . |
| 2099699 | 12/1982 | United Kingdom . |
| 2108517 | 5/1983 | United Kingdom . |

OTHER PUBLICATIONS

Journal of Pharmaceutical Sciences, vol. 72, No. 1, Jan. 1983, pp. 17–22, American Pharmaceutical Association; D. S. T. Hsieh et al.: "Zero-Order Controlled-Release Polymer Matrices for Micro- and Macromolecules" p. 17, abstract; p. 20, right-hand column.

Primary Examiner—Ronald W. Griffin
Attorney, Agent, or Firm—Oblon, Fisher, Spivak, McClelland & Maier

[57] ABSTRACT

A controlled release device which comprises:
  (i) a hydrogel; and incorporated therewith
  (ii) an active substance,
at least part of at least one surface of the device comprising
  (iii) a layer which is impermeable to aqueous media.

20 Claims, 7 Drawing Sheets

CONTROLLED RELEASE DEVICE

This application is a continuation of application Ser. No. 889,309, filed on July 28, 1986, now abandoned, which is a continuation of application Ser. No. 633,459, filed July 23, 1984, abandoned.

This invention relates to controlled release devices. More particularly, this invention relates to controlled release devices having enhanced duration and/or control of active substance release.

In our GB Nos. 2047093B and 2047094B we have described controlled release compositions which comprise an active substance and a polymeric carrier therefor comprising residues having a ratio of number average molecular weight to functionality greater than 1,000 which comprise polyethylene oxide and are cross-linked through urethane groups. In many therapeutic and prophylactic medications it can be advantageous to provide a constant rate of delivery of the medication to the patient, so-called zero order release, sustained over a prolonged period of time. A number of active substances have been found to realise this aim when incorporated in controlled release compositions as aforesaid.

However, the release profile of an active substance from an initially dry hydrogel depends, in a complex manner, on a number of parameters including the physiochemical properties of the active substance; in particular, both its solubility characteristics and molecular size in the eluting medium; the geometry of the hydrogel; and the physiochemical properties of the hydrogel; in particular, both its rate of swelling and equilibrium swelling of the device in the eluting medium at the temperature of diffusion. It has been found that the release profiles of active substances with good solubility in the eluting medium, for example an aqueous medium, from initially dry hydrogels, for example hydrogels comprising polyethylene oxide, with an equilibrium swelling of 200 pph or more and of a size suitable for administration are not constant; rather, the release rates are initially large and gradually fall during a less sustained period of time.

This invention is of particular, but not exclusive, relevance to the treatment of the sexually transmitted disease caused by the virus Herpes Simplex II. At the present there is no effective therapy for this disease although the virus and/or its replication is known to be destroyed by addition of lithium salts. However, lithium salts are both very soluble and are also rapidly excreted from the body.

This invention seeks to provide an improved controlled release device of broad applicability to swellable hydrogels wherein a greater degree of control over the release profile of an active substance therefrom is obtained. This invention also seeks to provide effective lithium salt medication, especially in combating Herpes Simplex II virus.

According, therefore, to one aspect of this invention, there is provided a controlled release device which comprises:
(i) a hydrogel; and incorporated therewith
(ii) an active substance
at least part of at least one surface of the device comprising
(iii) a layer which is effectively impermeable to aqueous media.

The hydrogel (i) can comprise a natural or synthetic organic or inorganic material (for example, silica gel). It is preferred, by reason of the greater degree of control which can be achieved by tailoring the hydrogel structure, that the hydrogel is of an organic material. It is also preferred, by reason of the greater reproducibility, that the hydrogel is a synthetic material.

Examples of natural organic materials include crosslinked bio-polymers; for example, crosslinked polysaccharides such as starches, dextrans and celluloses; crosslinked proteins or polypeptides such as collagen and gelatin.

Suitably the hydrogel comprises a synthetic hydrophilic homo- or copolymer comprising residues derivable from at least one of the following monomer classes:
(a) (meth)acrylic acid, (meth)acrylamide, an unsubstituted or hydroxy-substituted, propyl, ethyl, or other alkyl (meth)acrylate or a poly(oxyethylene) (meth)acrylate;
(b) a substituted or unsubstituted cyclic mono or poly ether having from 3 to 6 ring atoms or cyclic imine having 3 ring atoms; or
(c) a substituted or unsubstituted vinyl alcohol, aldehyde, ether, acetal, ketone, ester, anhydride or substituted or unsubstituted N- or C- vinyl heterocyclic compound.

By "(meth)acryl" we mean herein "methacryl" or "acryl" or a copolymer comprising both.

Monomers in class (b) include epoxides such as ethylene oxide, propylene oxide, 1,2-epoxybutane, 2,3-epoxybutane glycidyl ethers, N-(epoxy substituted) heterocyclic compounds such a N-(2,3-epoxypropyl)-pyrrolidone; epihalohydrins, while not themselves cyclic ethers, do give homo- and copolymers derivable therefrom; examples include epifluorohydrin, epichlorohydrin and epibromohydrin. Other cyclic mono- or poly ethers include oxetane, tetrahydrofuran, dihydropyran, dioxolane and trioxane. Homo- and copolymers derivable therefrom include partially $C_1$ to $C_4$ alkyl etherified celluloses and starches, homo- and co-poly(alkylene oxides) such as polyoxymethylene, polyethylene glycols and polypropylene glycols, and polyesters thereof with dicarboxylate acids such as maleic acid which may be cross-linked through reaction with isocyanate or unsaturated cyclic ether groups.

Monomers in class (c) include methyl and ethyl vinyl ether, methyl vinyl ketone, methallyl alcohol, maleic anhydride, N-vinyl pyrrolidone, N-vinyl carbazole, C-vinyl pyridine, N-vinyl oxazole, N-vinyl methyloxazolidone, vinyl formal, vinyl butyral, vinyl methoxyacetal. Homo- and copolymers derivable therefrom include polyvinyl acetate and polyvinyl alcohol.

The synthetic hydrophilic homo- or copolymer may be chemically cross-linked to form the hydrogel. A general process for accomplishing this in a very satisfactory manner and resulting in a finely divided hydrogel is disclosed in our GB No. 2090264B. Where the hydrophilic polymer comprises functional groups which comprise an active hydrogen atom (for example, hydroxyl, amino, mercapto, carboxylic or phosphoric acid, amide, thiolic or thionic analogues) chemical cross-linking may be effected by reaction with a di- or poly-isocyanate (such as bis-(4-isocyanatophenyl) methane) or a di- or poly- linear or cyclic olefinically unsaturated ether (such as acrolein tetramer); for example, as disclosed in our GB No. 2047093B, GB No. 2047094B and copending application GB No. 2108517A, from which it will be apparent that where a diisocyanate or di-olefinically unsaturated ether is used a reactant comnprising at least three active hydrogen atoms must also be present to ensure chemical crosslinking.

Entanglement cross-linking may be utilised, especially where the hydrophilic polymer has a high molecular weight (for example, $\overline{M}_n$ greater than 20,000) by incorporating in the hydrophilic polymer and polymerising monomers of functionality greater than two. Examples of such monomers include di- and poly-olefinically unsaturated hydrocarbons, such as divinyl benzene or isoprene, and the di- and poly-olefinically unsaturated esters or ethers, such as acrolein tetramer, triallyl cyanurate or glycol dimethacrylate.

Block copolymers comprising both hydrophilic and hydrophobic domains (for example, ethylene oxide-higher alkylene oxide, such as propylene oxide, block copolymers) are also very suitable.

Preferably, the hydrogel (i) comprises a homo- or copoly(alkylene oxide), preferably poly(ethylene oxide). It is also preferred that the poly(alkylene oxide) is cross-linked through reaction with isocyanate or unsaturated cyclic ether groups. Very satisfactory examples of such hydrogels, and of their preparation, are disclosed in our aforementioned patents and patent applications.

The present invention is of broad applicability in the formulation of active substances (ii), particularly, but not exclusively, biologically active substances releasable for a sustained period of time. Examples of classes of biologically active substances which may be incorporated in controlled release devices of the present invention include flavourings, pharmaceuticals, bacteriostats, viruscides, pesticides such as insecticides, nematicides, molluscicides and larvicides, herbicides, fungicides, algaecides, topical or dermatological agents, antifoulants for marine growth prevention, proteins, for example enzymes, peptides, microbiological and plant hydroculture salts and nutrients and preservatives, veterinary trace metal formulations, and other growth promoting factors used in animal husbandry: for example, anti-anaemia preparations and anabolic steroids. Of particular interest is a device of the present invention comprising, as biologically active substance, at least one pharmaceutical.

The devices of this invention thus find wide application in medical and surgical, including veterinary, contexts and in horticulture and agriculture as well as outside these areas.

Specific classes of drug which may be utilised in a controlled release device of the invention include abortifacients such as prostaglandins, hypnotics, sedatives, tranquilisers, anti-pyretics, anti-inflammatory agents, anti-histamines, anti-tussives, anti-convulsants, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, preparations containing various substances for the treatment of infection of pathogens including anti-fungal agents, for example metronidazole, anti-parasitic agents and other anti-microbials, anti-malarials, cardiovascular agents, preparations containing hormones, for example endrogenic, estrogenic and progestational hormones, notably steroids such as oestradiol, sympathomimetic agents, hypoglycaemic agents, contraceptives, nutritional agents, preparations containing enzymes of various types of activity, for example chymotrypsin, preparations containing analgesics, for example aspirin, and agents with many other types of action including nematocides and other agents of veterinary application. Mixtures of active substances may be incorporated into the controlled release device.

The controlled release devices of this invention may be used as a contraceptive device suitably containing, as active substance, at least one natural or synthetic steroid sex hormone for example an oestrogen or progestogen. Suitably progestogens include the natural progesterone and its synthetic analogues, including 11-dehydroprogesterone, delalutin, 21-fluoro-17-acetoxy-6-α-methylprogesterone, medroxyprogesterone acetate, magestrol acetate, chlormadinone acetate, ethisterone, dimethisterone, A-norprogesterone, 19-norprogesterone, 21-norprogesterone, normethandrone, norethynodrel, norethindrone and its acetate, DL- and D-norgestrel, norgestrienone, ethynodiol diacetate, lynstrenol, ethynylestradiol, retroprogesterone, dydrogersterone, norvinodrel, quingestranol acetate, norethisterone and its acetate and oenanthate, anagesterone acetate, medrogestone, clomagestone, allyl estrenol and cingestol, preferably progesterone. Suitably oestrogens include the natural β-oestradiol and its synthetic analogues, principally ethinyloestradiol or mestranol, preferably β-oestradiol.

The controlled release devices of this invention are also useful in the treatment of diabetes and pernicious anaemia where, for example, the controlled release of insulin and cobalamin, respectively, may be utilised.

Moreover, the controlled release devices of this invention are particularly suited to treatment, both prophylactic and therapeutic, of tropical diseases; for example malaria, leprosy, schistosomiasis and clonorchiasis. Examples of drugs which can be used as biologically active substance in controlled release devices of this invention for the treatment of these and other tropical diseases include quinine, sulphonamides, rifamycin, clofazimine, thiambutasine, chlorphenyl derivatives, chlorguamide, cycloguanil, pyrimethamine, sulphadiazine, trimethoprim, quinoline derivatives such as pamaquine, chloroquine, pentaquine, primaquine and amodiquine, pararosaniline, sulphamethizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

The controlled release devices of this invention are also very well suited to veterinary applications. Examples include preparations of antibiotics for general antibacterial activity and also in the treatment of anaplasmosis in cattle; preparations for provision of a wide spectrum of activity against both ectoparasites, for example termites and endoparasites including arthropods, arrested larvae stages of nematodes, lungworms and general strongyles: these may comprise avermectins; preparations for provision of activity against tremotode, cestode and roundworm infections: these may comprise amoscanate and praziquantel: preparations for provision of activity against theileria in cattle: these may comprise biologically active naphthoquinones such as menoctone; preparations for provision of activity against babesiosis in cattle, horses and dogs: these may comprise berenil, amidocarb and diampron; preparation for provision of activity against liver fluke in sheep and cattle and against Haemonchus species: these may comprise closantel.

In accordance with a particularly preferred feature of this invention there is provided a controlled release device for the treatment of the Herpes Simplex II virus wherein the active substance is a lithium compound, preferably a lithium salt, especially a soluble lithium salt such as a lithium halide, for example lithium chloride.

In accordance with another preferred feature of this invention, there is provided a controlled release device for release of prostaglandins. Such controlled release devices can have a variety of effects on the body; for example, they may be useful in the treatment of schizophrenia, particularly $PGE_1$. They are, however, or particular interest in their action upon the female reproductive system of both human and non-human animals. By that action the controlled release compositions of this invention have found use as abortifacients; in the induction of labour; in a contraceptive role; and in the treatment of cervical incompetence, particularly in administration prior to artificial insemination in non-human animals. Both naturally-occuring and synthetic analogues of prostaglandins are of interest.

The natural prostaglandins of importance in reproduction are those of the E and F groups (for example $PGE_1$, $PGF_{1\alpha}$, $PGE_2$, $PGF_{2\alpha}$, $PGE_3$ and $PGF_{3\alpha}$), $PGI_2$ (prostacyclin) the compounds $PGE_2$ and $PGF_{2\alpha}$ being of particular interest. Examples of synthetic prostaglandins (analogues) include particularly derivatives of $PGE_2$ and $PGF_{2\alpha}$, specific derivative of clinical promise being 15-methyl-$PGF_2$, $PGF_{2\alpha}$, 16, 16-dimethyl-$PGE_2$, and also 16, 16-dimethyl-$PGE_2$ parabenzaldehyde semicarbazone ester, 16-phenoxy-17, 18, 19, 20-tetranor-$PGE_2$ and especially 16, 16-dimethyl-trans $\Delta^2$-$PGE_1$ which may very suitably be formulated according to the present invention, for example in the form of an ester such as the methyl ester. Particular prostaglandins may of course be of especial interest for particular applications so that $PGE_2$, for example, is of more interest in the induction of labour whilst 16, 16-dimethyl trans $\Delta^2$-$PGE_1$ is of more interest in inducing abortion. It will be appreciated that the invention will be applicable to subsequently prepared novel prostaglandin derivatives having similar but modified properties, for example greater potency, prolonged action, greater specificity, to those at present known and used as abortifacients. Thus, for example, there is considerable interest in "luteolytic" prostaglandins such as 16-(3-trifluoromethylphenoxy)-17, 18, 19 20-tetranor-$PGF_{2\alpha}$ and their use in a contraceptive role. It will be appreciated that, if desired, the polymeric carrier may incorporate two or more prostaglandins.

By "incorporated therewith" is meant herein that the active substance (ii) may be homogeneously or inhomogeneously dispersed throughout the hydrogel (i) or may be contained in a reservoir within the hydrogel or, indeed, both.

The controlled release devices of the invention may be formed in a variety of configurations; for example, one which is as a rod, slab, film, hemisphere or is of a hollow or periodic, for example sinusoidal, profile.

The impermeable layer (iii) is preferably hydrophobic; it is preferably also impermeable to the active substance (ii). Suitably, the impermeable layer (iii) covers all of at least one surface, preferably a curved surface, of the device thereby defining at least one orifice thereon through which the hydrogel (i) is contactable by aqueous media. Where the device is formed as a rod, slab or film the impermeable layer may cover substantially all of the surfaces except one or both end profiles (that is the surfaces usually, but not necessarily, substantially planar and of smallest area) the or each of which end profiles defines an orifice. Such a device, especially one comprising only one orifice, has a much longer half-life of release than like devices without the impermeable layer. Where the device is formed with a single or bis-sinusoidal profile along its length (the first sinusoidal profile may be reflected or out of phase with the second) the impermeable layer may cover substantially all of the surfaces except one or both end profiles. Such a device, especially one comprising only one orifice, exhibits a pulsatile release rate. Where the device is formed as a hemisphere, the impermeable layer can cover substantially all of the surfaces except a polar orifice in which case the device will provide a very prolonged release, the rate of which will either increase or remain constant with time. Where the entire curved surface of such a device is covered by the impermeable layer with the equatorial surface uncovered as the orifice the rate of release decreases with time.

The device may also be formed as a ring of hydrogel with the impermeable layer covering all the surfaces except the internal, typically cylindrical, surface which acts as the orifice. Such a device can provide a longer half-life of release and exhibit a rate of release which is constant or increases with time.

Furthermore, a multiplicity of orifices, for example, in a layer which substantially completely covers the device which may be formed as a rod enables a very precise regulation of half-life of release.

All of the aforementioned exemplary devices may be produced by simple technology. Thus, hydrogel for the cylindrical and slab devices may be moulded or continously produced by reactive extrusion. The hydrogel may then be dip coated (a plurality of coats may be provided) in an organic solution of a thermoplastic elastomer or sleeved with a preformed silicone, natural or synthetic polydienes or butyl elastomers and then sliced to the desired dimensions, the slicing exposing one or two orifices. The sleeving may be facilitated by incorporating a swelling agent in the sleeve or, in a preferred embodiment especially in relation to rods or slabs, deforming the hydrogel in accordance with our copending application. The hydrogel for the hemispherical and sinusoidal devices may be moulded, coated (preferably by dip coating) and cut in an essentially similar manner. The hemispheres may be moulded in tandem via a sprue which, after coating, is cut to expose a polar orifice in each hemisphere. The orifice may also be formed by lasing the fully coated device. The hydrogel for the ring device may be initially formed as a rod, which is then sliced, coated and, thereafter has an axial hole punched therethrough.

Spray and powder coating technology may also be utilised to form the impermeable coatings which apart from the aforementioned, may comprise drying oils, alkyds, urethanes, acrylics, and epoxides. In situ curing may be used, enhanced by thermal, UV or electron beam irradiation in known manner.

The devices of this invention exhibit a much longer half-life of release than like devices without the impermeable layer. This valuable attribute may be used as such or may be utilised to reduce the size of the dosage form, or indeed both. It will be seen, therefore, that the devices are particularly suited to formulating oral dosage forms.

COMPARATIVE EXAMPLE

A polyethylene oxide hydrogel was prepared essentially as described in Example 1 of GB No. 2047093A by reacting 1 mole of polyethylene oxide ($\overline{M}_n = 8,300$) with 0.75 mole of 1,2,6-hexanetriol and 2.125 moles of bis-(4-isocyanatocyclohexyl)methane. The hydrogel was found to have an equilibrium swelling in water, at 20° C., of 400 pph, based on the initial dry weight of hydrogel.

Three cylinders of the hydrogel, 6 mm in diameter and 15 mm in length, were cast. The first was sliced into 20 discs each approximately 0.75 mm thick; the second was cut into 6 pieces each approximately 2.5 mm thick; and the third was kept intact. The 20 discs, 6 pieces and intact cylinder were next swollen in a 4 mg ml$^{-1}$ LiCl solution and dried. Three size 0 hard gelatin capsules were respectively packed with the 20 discs, 6 pieces and intact cylinder; and capped.

To simulate oral dosing, the loaded capsules were separately immersed in 0.01N hydrochloric acid at 37° C. and shaken at 200 vibrations per minute in a Grant Shaking Thermostat Bath at 37° C. A fourth gelatin capsule comprising a small amount of methyl violet was also immersed in the hydrochloric acid to ascertain the time to disintegration of the capsule (which was found to 10 minutes). Aliquots of the hydrochloric acid were removed periodically and their lithium content was determined by atomic absorption spectroscopy (Perkin Elmer 360 atomic absorption spectrophotometer). The hydrochloric acid removed was initially replenished by fresh 0.01N hydrochloric acid at 37° C. and, after the first hour, by distilled water at 37° C.

Figure 1:
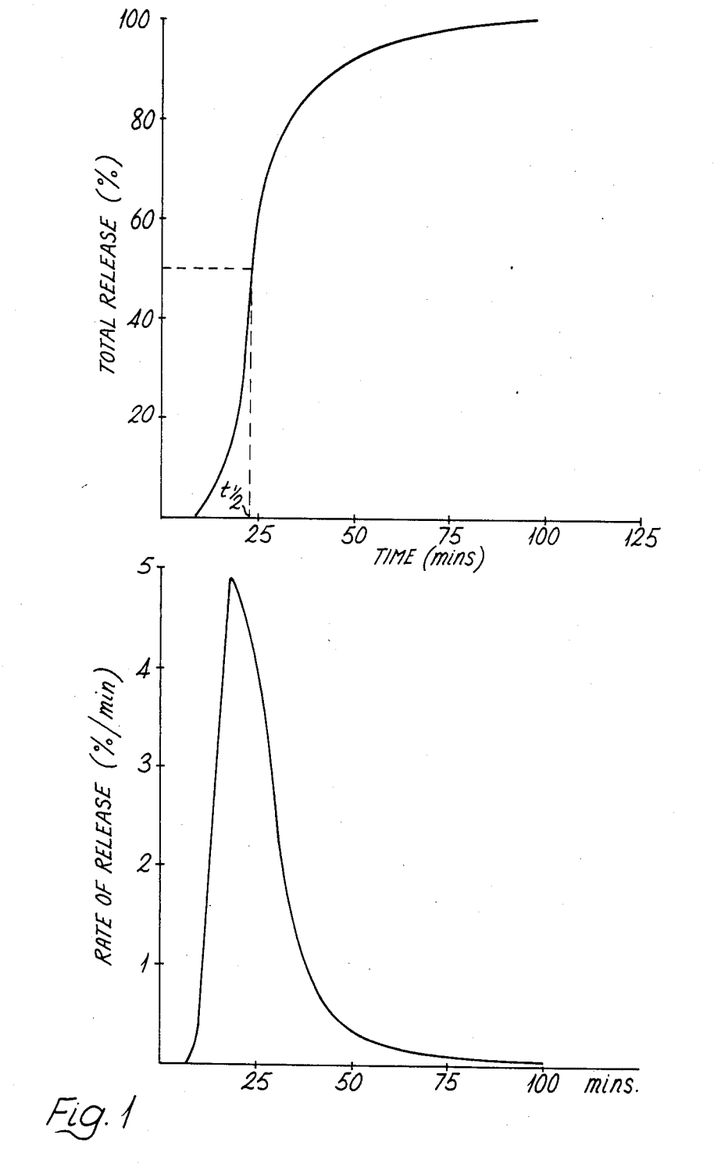
Figure 2:
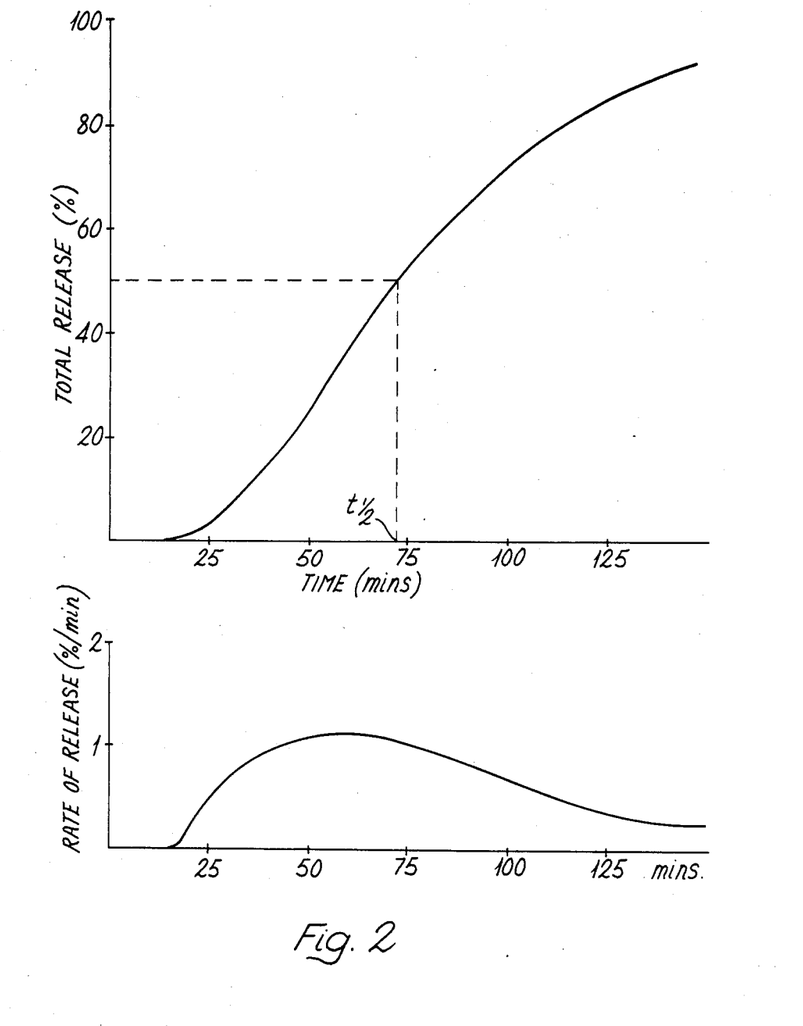
Figure 3:
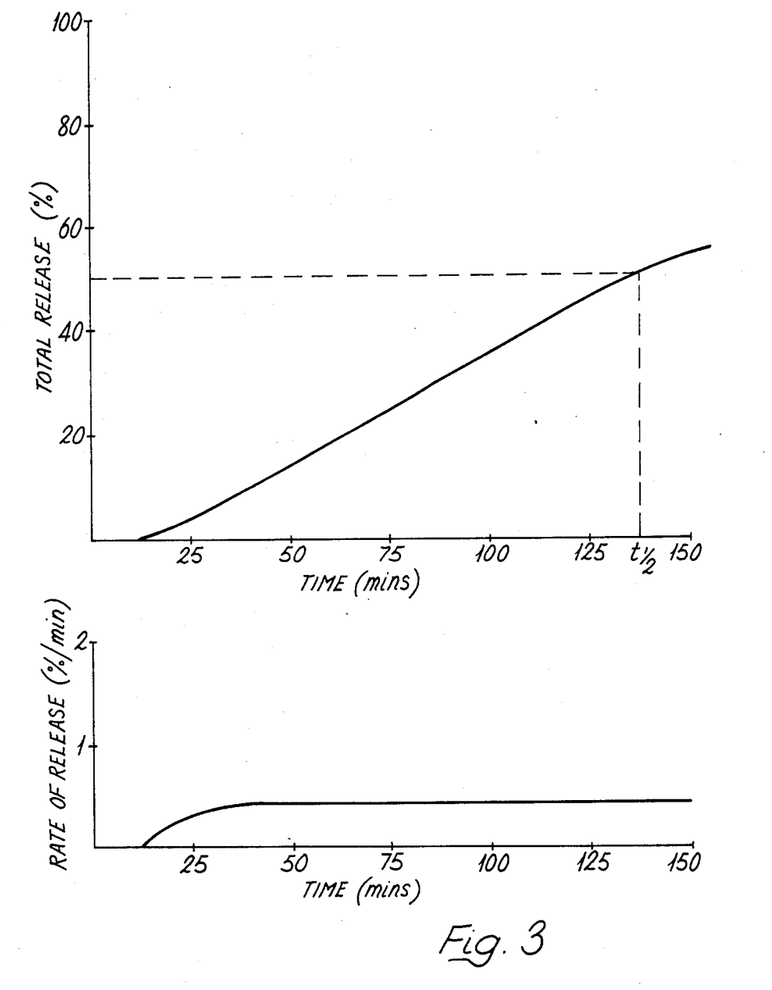

The results are shown in FIGS. 1 to 3 of the accompanying drawings.

The following Examples illustrate the invention.

Examples 1 to 3, inclusive, illustrate the preparation of controlled release reservoir devices of the invention in an attempt, successfully realised in Example 3, to secure release of approximately 1 g of lithium chloride at a substantially constant rate over a one week period. In all cases where plugs were not retained by means other than friction, the high osmotic pressure expelled them, vitiating the experiments (not exemplified).

EXAMPLE 1

Two polyethylene oxide hydrogels were prepared essentially as described in Example 1 of GB No. 2047093B by reacting, in a first case, 1 mole of polyethylene oxide ($\overline{M}_n = 3,207$) with 1 mole of 1,2,6-hexanetriol and 2.5 mole of bis-(4-isocyanatocyclohexyl) methane; and, in a second case, 1 mole of the same polyethylene oxide with 2 moles of of 1,2,6-hexanetriol and 4 moles of bis-(4-isocyanatocyclohexyl)methane.

A blank hollow cylinder of the seocnd hydrogel, 12 mm in external diameter, 6 mm in internal diameter, 3 mm in basal thickness and 30 mm in length, was cast. An internal annular groove was then machined from the cylinder near its mouth and its cavity was packed with 1 g of lithium chloride crystals. The first hydrogel was next cast as a plug mating with the annular groove and which, due to its higher swelling, would become tighter on swelling. The resulting cylindrical reservoir was then sheathed with tight-fitting silicone rubber tubing ("Silescol" translucent silicone rubber tubing ex Esco (Rubber) Ltd.) which had a bore of 8 mm and a wall thickness of 1.6 mm. The tubing was first softened by swelling in diethyl ether for 5 minutes whereupon it was readily possible to insert the hydrogel cylinder into the swollen tube. Thereafter, the diethyl ether was expelled by rapid evaporation in a laminar flow cabinet and then in vacuo. The silicone rubber was 8 mm longer than the cylinder to keep the curved wall of the cylinder covered during swelling; it also contained 16 small (about 2.0 mm in diameter) holes linearly punched therein and evenly spaced apart.

The controlled release reservoir device so formed was immersed in distilled water at 37° C. in a thermostated shaking bath at the same temperature in order to avoid a build-up of a static layer of lithium chloride around the device. Aliquots of the water were removed periodically and their lithium content was determined by atomic absorption spectroscopy.

Figure 4:
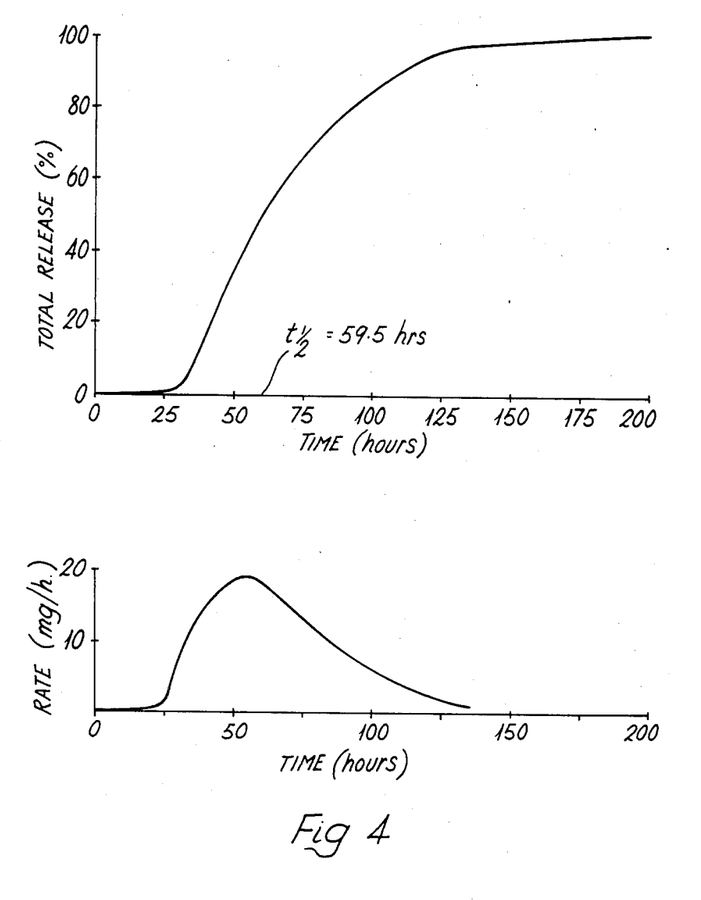

The results are shown in FIG. 4 of the accompanying drawings.

EXAMPLE 2

A size 0 hard gelatin capsule was packed with lithium chloride crystals; capped; and suspended axially and centrally by a nylon thread in a polyethylene vial, 12 mm in internal diameter and 55 mm in length, which acted as a mould. An amount of the second reactant mixture mentioned in Example 1 was then cast into the mould around the capsule. The cylinder (12 mm × 50 mm) was removed from the mould by making radially-opposed, axial cuts in the vial and stripping the vial therefrom; and next sheathed with tight-fitting silicone rubber tubing as described in Example 1, except that it contained only 8 small holes.

Figure 5:
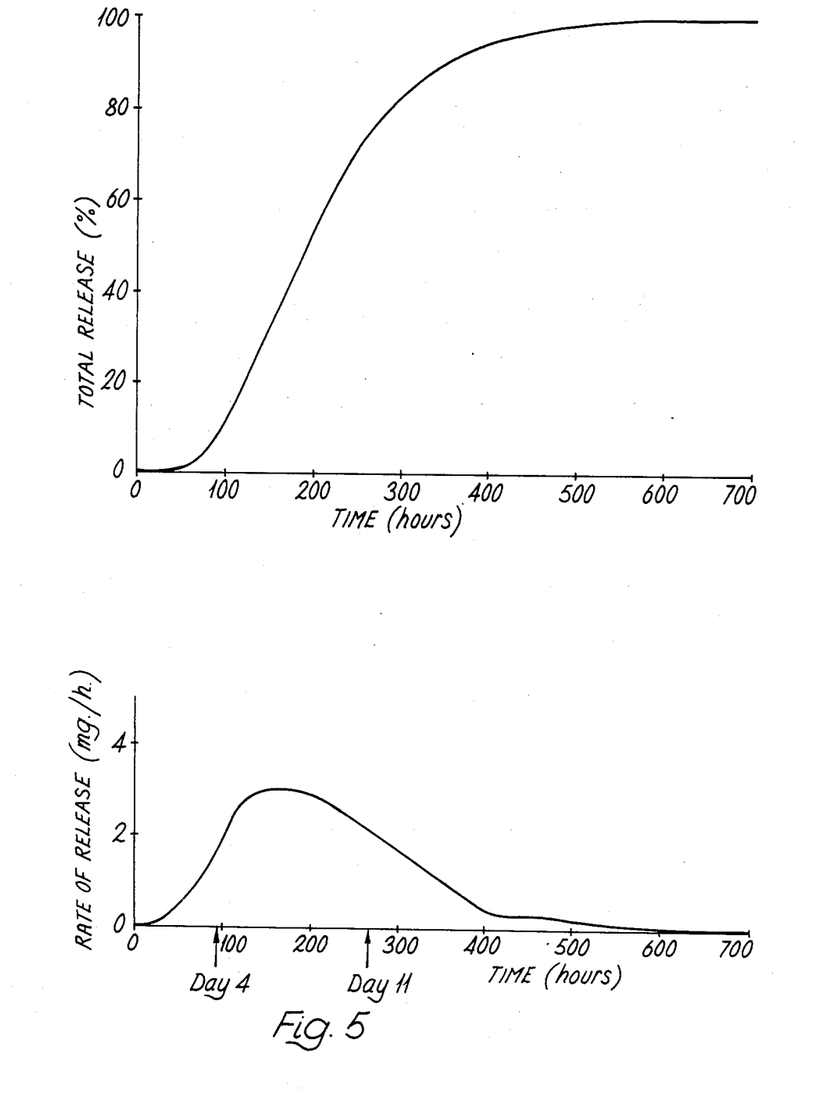

The controlled release reservoir device so formed was then tested as described in Example 1 and the results were shown in FIG. 5 of the accompanying drawings.

EXAMPLE 3

Two size O hard gelatin capsules were packed with a total of 1 g lithium chloride crystals; capped; and inserted into a blank, hollow cylinder of the second hydrogel as described in Example 1. A separately cast plug of the first hydrogel in Example 1 was inserted in the cylinder and retained by a steel pin radially driven through both cylinder and plug. The cylinder was then sheathed with tight-fitting silicone rubber tubing as described in Example 2.

Figure 6:
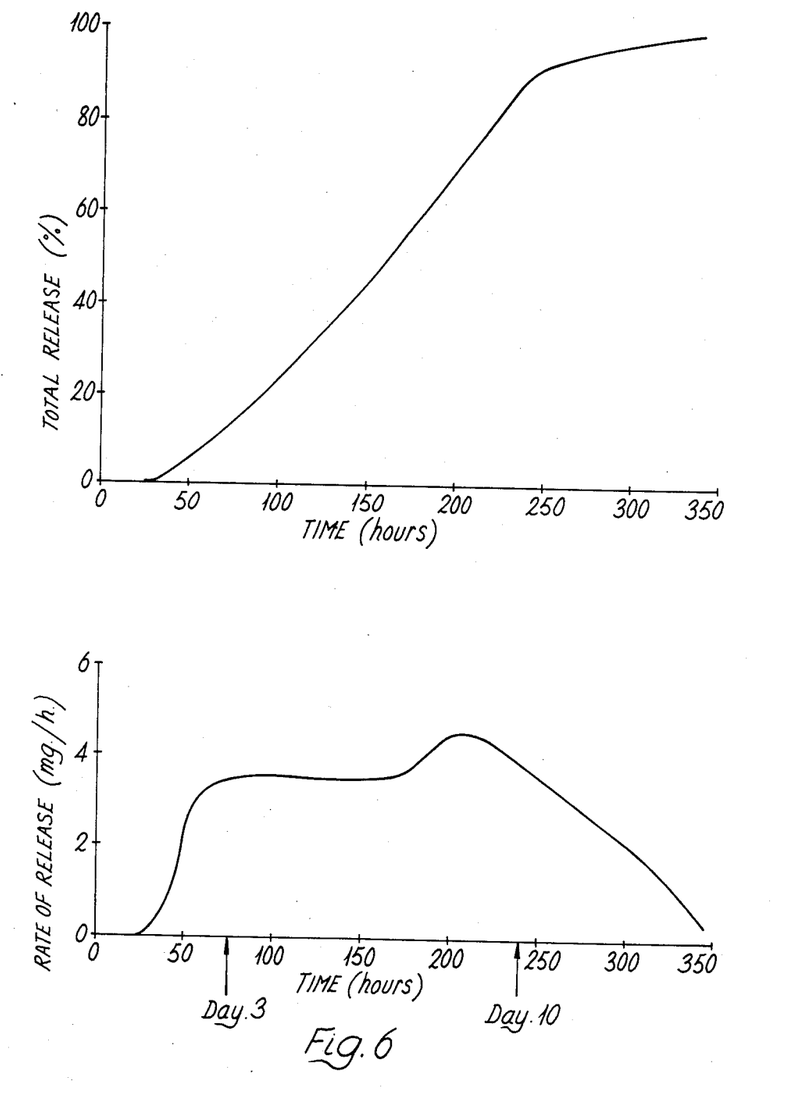

The controlled release reservoir device so formed was then tested as described in Example 1 and the results were shown in FIG. 6 of the accompanying drawings.

Example 4 illustrates the preparation of a controlled release reservoir device comprising a hydrogel of a lower equilibrium swelling in water than is the case in Example 1 to 3 and wherefrom plugs are found not be expelled on swelling.

EXAMPLE 4

A polyethylene oxide hydrogel was prepared essentially as described in Example 1 by reacting 1 mole of polyethylene oxide ($\overline{M}_n = 3,330$) with 4 moles of 1,2,6-hexanetriol and 7 moles of bis-(4-isocyanatocyclohexyl)methane. The hydrogel was cast to form a blank, hollow cylinder 12 mm in external diameter, 6 mm in internal diameter, 4 mm in basal thickness and 50 mm in length. The cylindrical cavity was then packed with 1 g lithium chloride crystals and a plug of the same hydrogel 6 mm in diameter and 6 mm in length was tightly inserted. The resulting cylindrical reservoir was then sheathed as in Example 2.

The controlled release reservoir device so formed was immersed in distilled water at 37° C. in a Grant Shaking Thermostat Bath. The release medium was removed daily (being replaced by distilled water at 37°) for determination of its lithium content by atomic absorption spectroscopy.

Figure 7:
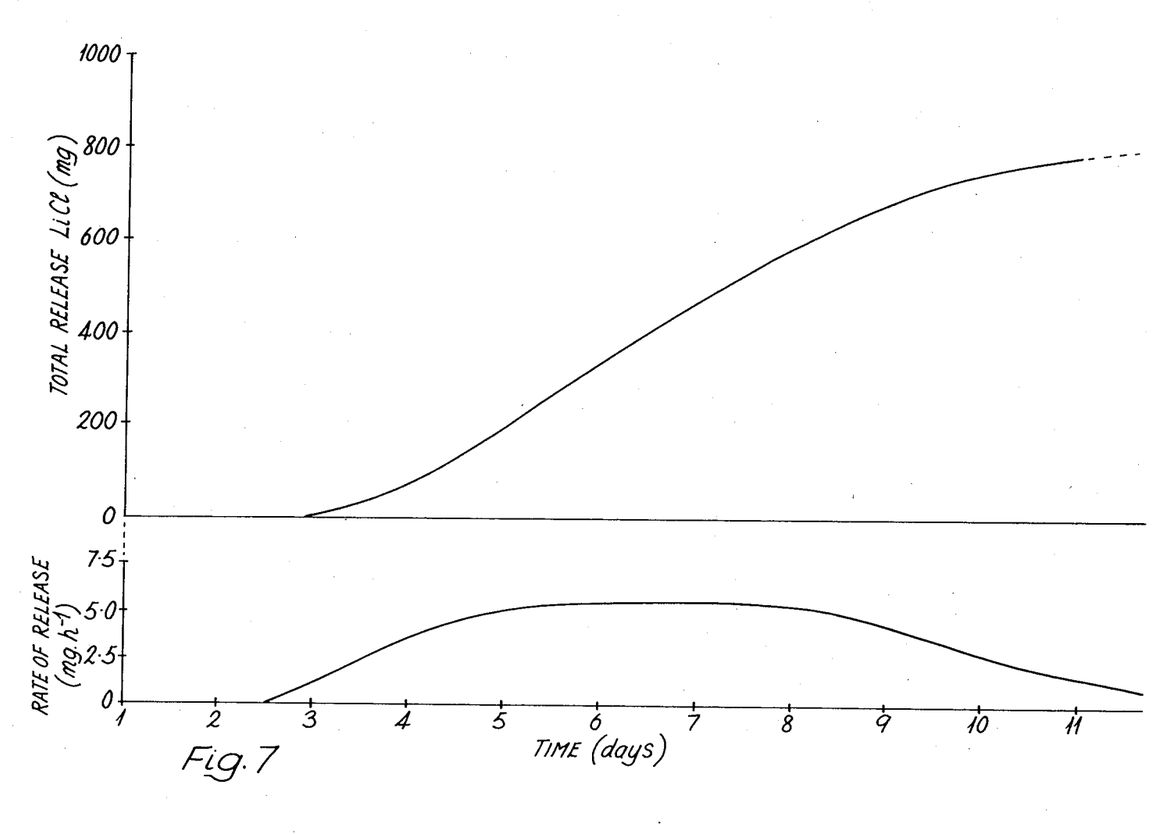

The results are shown in FIG. 7 of the accompanying drawings. It will be seen that lithium first appeared in the release medium on day 3; thereafter a uniform release rate is established in day 4 which persists into day 9 by which time 70% of the total lithium chloride had been released.

EXAMPLE 5

A polyethylene oxide hydrogel was prepared essentially as described in Example 1 by reacting 1 mole of polyethylene oxide ($\overline{M}_n=8,400$) with 0.75 mole of 1,2,6-hexanetriol and 2.125 moles of bis-(4-isocyanatocyclohexyl)methane. The hydrogel was found to have an equilibrium swelling (weight gain) in water, at 37° C., of 292 pph.

The hydrogel was cast to form a mass 10 mm×30 mm×40 mm which was then cut into slabs each 10 mm×30 mm×1.35 mm which were next trimmed to provide slabs each 10 mm×22 mm×1.35 mm and whose profiles had rounded ends. The slabs were swollen in a 0.1M p-aminobenzoic acid aqueous solution containing 0.1M ammonia at 37° C. After equilibrium was attained the swollen slabs were dried at room temperature under vacuum to constant weight. A 10% w/v solution of a thermoplastic rubber (Cariflex TR-1101 ex Shell chemicals) was next prepared in chloroform. The dried slabs were dip coated in this solution; dried in air at room temperature; and the process was repeated as required until a tough, water-impermeable coating had accreted. The coated slabs were then cut to 20 mm lengths removing the semi-circular coated ends and leaving both ends of 10 mm breadth and 1.35 thickness uncoated to form a controlled release device. Typically each such device weighed about 300 mg and contained about 12.0 mg of p-aminobenzoic acid.

The controlled release device so formed was immersed in 1000 ml of a simulated intestinal fluid (6.8 g $KH_2PO_4$, 38 ml 1M NaOH per liter, adjusted to pH 7.5) in metal baskets which were rotated at 100 rpm. The release of p-aminobenzoic acid was determined by measuring the increase in the ultra-violet absorption at 264 mm at hourly intervals.

The results are shown in Table 1.

EXAMPLE 6

Hydrogel slabs prepared essentially as described in Example 5 were swollen in a 0.4% w/v solution of benzocaine in chloroform and dried at room temperature under vacuum to constant weight. The dried slabs were then dip coated as described in Example 5. Typically, each such controlled release device contained about 9.0 mg of benzocaine.

Release and determination procedure was essentially as described in Example 5; the results are shown in Table 2.

TABLE 2

Release of benzocaine from coated hydrogel devices of slab geometry

| | a Uncoated control | | b 3 Coats | |
|---|---|---|---|---|
| Time (Hour) | % Release per hour | Cumulative Release (%) | % Release per hour | Cumulative Release (%) |
| 1 | 45 | 45 | 7 | 7 |
| 2 | 31 | 76 | 10 | 17 |
| 3 | 12 | 88 | 10 | 27 |
| 4 | 6 | 94 | 9 | 36 |
| 5 | 3 | 97 | 8 | 44 |
| 6 | 1 | 98 | 8 | 52 |
| 7 | 0 | 98 | 8 | 60 |

EXAMPLE 7

In this Example the variation of release with the length of controlled release devices essentially as described in Example 5 is described. Hydrogels slabs prepared, swollen and dried essentially as described in Example 5 were then given three dip coatings and cut to lengths to 6 mm, 10 mm or 20 mm. Typically, such a controlled release device 20 mm in length contained about 140 mg of p-aminobenzoic acid.

Release and determination procedure was essentially as described in Example 6; the results are shown in Table 3.

TABLE 3

Effect of length of coated device on duration of release

| | Coated 0.6 cm | | Coated 1.0 cm | | Coated 2.0 cm | |
|---|---|---|---|---|---|---|
| | Amount released (mg) | % released | Amount released (mg) | % released | Amount released (mg) | % released |
| 1 | 9.7 | 20 | 9.8 | 14 | 10.1 | 7 |
| 2 | 19.2 | 42 | 18.3 | 27 | 19.3 | 14 |
| 3 | 27.0 | 59 | 28.1 | 41 | 29.1 | 21 |
| 4 | 29.8 | 65 | 33.9 | 50 | 35.3 | 25 |
| 5 | 33.0 | 72 | 38.5 | 57 | 39.9 | 28 |
| 6 | 34.7 | 76 | 42.2 | 62 | 43.8 | 31 |
| 7 | 37.5 | 82 | 45.8 | 67 | 47.2 | 38 |

EXAMPLE 8

A polyethylene oxide hydrogel was prepared essentially as described in Example 1 by reacting 1 mole of polyethylene oxide ($M_n=7,000$) with 2 moles of 1,2,6-hexanetriol and 4 moles of bis-(4-isocyanatocyclohexyl)methane. The hydrogel was found to have an equilib-

TABLE 1

Release of p-aminobenzoic acid from coated hydrogel devices of slab geometry

| | a Uncoated control | | b 3 Coats | | c 5 Coats | |
|---|---|---|---|---|---|---|
| Time (Hours) | % Release per hour | Cumulative Release (%) | % Release per hour | Cumulative Release (%) | % Release per hour | Cumulative Release (%) |
| 1 | 75 | 75 | 13 | 13 | 10 | 10 |
| 2 | 25 | 100 | 14 | 27 | 10 | 20 |
| 3 | — | 100 | 16 | 43 | 12 | 32 |
| 4 | — | 100 | 12 | 55 | 11 | 43 |
| 5 | — | 100 | 13 | 68 | 11 | 54 |
| 6 | — | 100 | 9 | 77 | 9 | 63 |
| 7 | — | 100 | 4 | 81 | 7 | 70 | rium swelling (weight gain) in water, at 37° C., of 215 pph. The hydrogel was cast to form a cylinder 500 mm in length and 6 mm in diameter. The cylinder was then swollen and dried essentially as described in Example 5, and cut into 10 mm lengths. Some of these lengths remained, as controls, uncoated; some were given four dip coatings as described in Example 5 with one or both flat ends of the coating cut away; some were sheathed with silicone rubber tubing as described in Example 1 but cut to the length of the device and free from punched holes.

Release and determination procedure were essentially as described in Example 5; the results are shown in Table 4.

TABLE 4

Release of p-aminobenzoic acid from coated hydrogel devices of cylindrical geometry

| Time (hour) | a Uncoated control | | b 4 coats both ends uncoated | | c Covered with silicone tubing both ends exposed | | d 4 coats one end uncoated | |
|---|---|---|---|---|---|---|---|---|
| | % Released per hour | Cumulative release (%) | % Released per hour | Cumulative release (%) | % Released per hour | Cumulative release (%) | % Released per hour | Cumulative release (%) |
| 1 | 28 | 28 | 16 | 16 | 13 | 13 | 7 | 7 |
| 2 | 15 | 43 | 11 | 27 | 8 | 21 | 5 | 12 |
| 3 | 11 | 54 | 9 | 36 | 7 | 28 | 5 | 17 |
| 4 | 9 | 63 | 6 | 42 | 5 | 33 | 3 | 20 |
| 5 | 7 | 70 | 7 | 49 | 5 | 38 | 4 | 24 |
| 6 | 5 | 75 | 5 | 54 | 4 | 42 | 3 | 27 |
| 7 | 5 | 80 | 6 | 60 | 5 | 47 | 3 | 30 |
| 24 | — | 99 | — | 95 | — | 76 | — | 67 |

EXAMPLE 9

A polyethylene oxide hydrogel was prepared essentially as described in Example 1 by reacting 1 mole of polyethylene oxide ($\overline{M}_n=7,000$) with 2 moles of 1,2,6-hexanetriol and 4 moles of bis-(4-isocyanato-cyclohexyl)methane. The hydrogel was cast to form a cylindrical mass 12 mm in diameter from which a number of discs 5 mm in height were cut. The discs were then swollen in a 0.1M p-aminobenzoic acid aqueous solution containing 0.1M ammonia at 37° C. After equilibrium was attained (194% weight gain) the swollen slabs were dried at room temperature under vacuum to constant weight.

A cylindrical hole 3.2 mm in diameter was next punched axially through the centre of each disc to produce an annular mass into the central channel of which a well-fitting steel rod was introduced. The annular masses were then each dip coated five times in a solution as described in Example 5. The steel rod was carefully removed leaving an annular controlled release device coated on the entire external surface but with an uncoated central channel 3.2 mm in diameter therethrough.

Release and determination procedures were essentially as described in Example 5; result as shown in Table 5.

TABLE 5

Release of p-aminobenzoic acid from externally coated devices of annular geometry

| Time (hour) | a Uncoated control | | b Coated devices | |
|---|---|---|---|---|
| | % Release per hour | Cumulative release (%) | % Release per hour | Cumulative release (%) |
| 1 | 17 | 17 | 3.5 | 3.5 |
| 2 | 14 | 31 | 3 | 6.5 |
| 3 | 11 | 42 | 3 | 9.5 |
| 4 | 10 | 52 | 3.5 | 13 |
| 5 | 9 | 61 | 2 | 15 |
| 6 | 7 | 68 | 3.5 | 18.5 |
| 7 | 6 | 74 | 2.5 | 21 |

TABLE 5-continued

Release of p-aminobenzoic acid from externally coated devices of annular geometry

| Time (hour) | a Uncoated control | | b Coated devices | |
|---|---|---|---|---|
| | % Release per hour | Cumulative release (%) | % Release per hour | Cumulative release (%) |
| 8 | 5 | 79 | 3 | 24 |

EXAMPLE 10

The preparation, release and determination procedures of Example 5 were followed except that the slabs were swollen in a 2% w/v aqueous solution of caffeine at 37° C. the results are shown in Table 6.

TABLE 6

Release of caffeine from coated hydrogel devices of slab geometry

| | | Cumulative release (%) | | | | |
|---|---|---|---|---|---|---|
| Time (hour) | a Uncoated control | b 3 Coats | | | c 2 Coats | |
| | | 20 mm | 10 mm | 5 mm | 8 mm | 4 mm |
| 1 | 75 | 11 | 18 | 28 | 26 | 47 |
| 2 | 96 | 20 | 35 | 55 | 48 | 76 |
| 3 | — | 28 | 53 | 70 | 65 | 90 |
| 4 | — | 36 | 72 | 81 | 76 | 97 |
| 5 | — | 42 | 81 | 87 | 83 | — |
| 6 | — | 47 | 86 | 91 | 87 | — |
| 7 | — | 52 | 90 | 94 | 91 | — |

¹Length of dried controlled release device.

This Example shows clearly the effect of the mechanical properties of the layer; thus, the more coats the more does the layer restrict the swelling of the hydrogel and items reduced the release of active substance.

EXAMPLE 11

A polyethylene oxide hydrogel was prepared essentially as described in Example 1 by reacting 1 mole of polyethylene oxide ($\overline{M}_n=4,360$) with 1 mole of 1,2,6-hexanetriol and 2.5 moles of bis-(4-isocyanatocyclohexyl)methane. The hydrogel was cast to form a cylindrical mass 6 mm in diamter from which cylindrical masses 5 mm or 10 mm in height were cut. The cylinders were then swollen in a 2% w/v aqueous solution of sodium p-aminobenzoate at 37° C. After equilibrium was attained (191% weight gain) the swollen cylinders were dried at room temperature under vacuum to constant weight.

Each such cylinder was next dip coated five times to produce a cylindrical controlled release device coated on its curved surface but with uncoated ends.

Release of the p-aminobenzoate was followed continuously by UV spectrometry. The results are shown in Table 7.

TABLE 7

Release of p-aminobenzoic acid from coated hydrogel of devices cylindrical geometry

| | a. Uncoated control | | b. Coated | | | |
|---|---|---|---|---|---|---|
| | | | 5 mm rod | | 10 mm rod | |
| Time (hour) | Cumulative release (%) | % Release per 2 hr interval | Cumulative release (%) | % Release per 2 hr interval | Cumulative release (%) | Release per 2 hr interval |
| 2 | 27.3 | 27.3 | 20.3 | 20.3 | 11.3 | 11.3 |
| 4 | 43.2 | 15.9 | 32.2 | 11.9 | 17.6 | 6.3 |
| 6 | 56.1 | 12.9 | 42.4 | 10.2 | 22.6 | 5.0 |
| 8 | 66.2 | 10.1 | 51.8 | 9.4 | 27.1 | 4.5 |
| 10 | 74.8 | 8.6 | 61.0 | 9.2 | 30.7 | 3.6 |
| 12 | 80.6 | 5.8 | 68.6 | 7.6 | 34.3 | 3.6 |
| 14 | 84.9 | 4.3 | 76.2 | 7.6 | 37.1 | 2.8 |
| 16 | 87.8 | 2.9 | 82.3 | 6.1 | 40.3 | 3.2 |
| 18 | 89.9 | 2.1 | 86.9 | 4.6 | 42.7 | 2.4 |
| 20 | 91.0 | 1.1 | 90.2 | 3.3 | 45.2 | 2.5 |
| 22 | — | — | 93.1 | 2.9 | 47.6 | 2.4 |
| 24 | — | — | 96.0 | 2.9 | 49.6 | 2.0 |

We claim:

1. A controlled release device, which comprises:
   (i) a hydrogel; and incorporated therewith
   (ii) an active substance which is released through the hydrogel, with at least part of at least one surface of the device comprising
   (iii) a layer which is impermeable to aqueous media and to said active substance thereby providing control of release of active substance from said device to the extent that at least functionally effective amounts of said active substance are released.

2. The controlled release device according to claim 1 wherein the hydrogel (i) comprises a hydrophilic homo- or copolymer comprising residues derivable from at least one of the following monomer classes:
   (a) (meth)acrylic acid, (meth)acrylamide or an unsubstituted or hydroxy-substituted alkyl (meth)acrylate or a poly(oxyethylene)(meth)acrylate;
   (b) a substituted or unsubstituted cyclic mono or poly ether having from 3 to 6 ring atoms or cyclic imine having 3 ring atoms; or
   (c) a substituted or unsubstituted vinyl alcohol, aldehyde, ether, acetal, ketone, ester, anhydride or substituted or unsubstituted N- or C- vinyl heterocyclic compound.

3. The controlled release device according to claim 1 or 2 wherein the hydrogel (i) comprises a homo- or copoly(alkylene oxide).

4. The controlled release device according to claim 3 wherein the hydrogel (i) comprises a poly(ethylene oxide).

5. The controlled release device according to claim 3 wherein the poly(alkylene oxide) is cross-linked through reaction with isocyanate or unsaturated cyclic ether groups.

6. The controlled release device according to claim 1 wherein the active substance (ii) comprises a lithium salt.

7. The controlled release device according to claim 1 wherein the active substance (ii) comprises a prostaglandin.

8. The controlled release device according to claim 1 wherein the active substance (ii) is homogeneously dispersed throughout the hydrogel (i).

9. The controlled release device according to claim 1 wherein the active substance (ii) is contained in a reservoir within the hydrogel (i).

10. The controlled release device according to claim 1 which is formed as a rod, slab, film hemisphere and/or is of hollow or sinusoidal profile.

11. The controlled release device according to claim 1 wherein the impermeable layer (iii) is hydrophobic.

12. The controlled release device according to claim 1 where the impermeable layer (iii) covers all of at least one surface of the device thereby defining at least one orifice thereon through which the hydrogel (i) is contactable by aqueous media.

13. The controlled release device according to claim 1 which comprises a rod, slab or film of hydrogel (i) wherein the impermeable layer (iii) covers all of the surfaces except one or both end profiles.

14. The controlled release device according to claim 1 wherein the rod or slab of hydrogel (i) is formed with a single or bis-sinusoidal profile along its length.

15. The controlled release device according to claim 1 which comprises a hemisphere of hydrogel (i) wherein the impermeable layer (iii) covers all of the surfaces except a polar orifice.

16. The controlled release device according to claim 1 which comprises a ring of hydrogel (i) wherein the impermeable layer (iii) covers all of the external surfaces.

17. The controlled release device according to claim 1, which contains a plurality of orifices which provide access to the hydrogel component through said impermeable layer.

18. The controlled release device according to claim 1, wherein the active substance (ii) is inhomogeneously dispersed throughout the hydrogel (i).

19. A controlled release device, which comprises:
   (i) a hydrogel, and incorporated therewith;
   (ii) an active substance which is released through the hydrogel, with at least one surface of the device comprising
   (iii) a layer which is impermeable to aqueous media and to said active substance, said layer having at least one orifice therein which provides access to said hydrogel component by said aqueous media and control of release of said active substance from said device.

20. A controlled release device, which comprises:
   (i) a hydrogel of a substituted or unsubstituted cyclic mono- or polyether having from 3 to 6 ring atoms; and incorporated therewith
   (ii) a lithium salt as an active substance which is released through the hydrogel, with at least a portion of at least one surface of the device comprising
   (iii) a layer which is impermeable to aqueous media and to said active substance thereby providing control of release of active substance from said device to the extent that at least therapeutically effective amounts of said lithium salt are released.

* * * * *